United States Patent [19]
Byram et al.

[11] Patent Number: 5,554,365
[45] Date of Patent: Sep. 10, 1996

[54] USE OF CYANOACRYLATE ADHESIVE COMPOSITIONS TO INHIBIT ACUTE RADIATION-INDUCED SKIN DAMAGE

[75] Inventors: Michael M. Byram, Colorado Springs, Colo.; Robert Goebel, Huntington Beach; Richard J. Greff, Yorba Linda, both of Calif.; Leonard V. Barley, Jr., Littleton, Colo.

[73] Assignee: MedLogic Global Corporation, Colorado Springs, Colo.

[21] Appl. No.: 435,590

[22] Filed: May 5, 1995

[51] Int. Cl.$^6$ ............................ A61K 31/74; A61K 31/78
[52] U.S. Cl. ............................................ 424/78.02; 514/528
[58] Field of Search ........................... 424/78.02; 514/528

[56] References Cited

U.S. PATENT DOCUMENTS

| | | |
|---|---|---|
| 3,722,599 | 3/1973 | Robertson et al. . |
| 5,254,132 | 10/1993 | Barley et al. . |
| 5,306,490 | 4/1994 | Barley et al. . |
| 5,403,591 | 4/1995 | Tighe et al. ............................. 424/445 |

FOREIGN PATENT DOCUMENTS

93/25196  12/1993  WIPO .

OTHER PUBLICATIONS

Sitton, *Early and Late Radiation–Induced Skin Alterations Part I: Mechanisms of Skin Changes*, Oncology Nursing Forum, 19(5):801–807 (1992).

Sitton, *Early and Late Radiation–Induced Skin Alterations Part II: Nursing Care of Irradiated Skin*, Oncology Nursing Forum, 19(6):907–912 (1992).

Dini, et al., *Management of Acute Radiodermatitis*, Cancer Nursing, 16(5):366–370 (1993).

Perez, et al., *Principles and Practice of Radiation Oncology*, Second Edition, J. B. Lippincott Company, Philadelphia, PA, pp. 104–105 (1987).

Rubin et al., *Skin and Adnexa*, Clinical Radiation and Pathology, Chapter 3, pp. 62–119 (1986).

*Primary Examiner*—Joseph L. Schofer
*Assistant Examiner*—Wu C. Cheng
*Attorney, Agent, or Firm*—Burns, Doane, Swecker & Mathis

[57] ABSTRACT

Disclosed are methods for inhibiting acute and/or late radiation/induced skin damage during treatment of a patient with ionizing radiation by application of a layer of cyanoacrylate adhesive to the skin surface prior to exposure of the surface to ionizing radiation.

22 Claims, No Drawings

USE OF CYANOACRYLATE ADHESIVE COMPOSITIONS TO INHIBIT ACUTE RADIATION-INDUCED SKIN DAMAGE

BACKGROUND OF THE INVENTION

1. Field of the Invention

This invention is directed to methods for inhibiting acute radiation-induced skin damage during treatment of a patient with ionizing radiation. Specifically, the methods of this invention involve application of a layer of cyanoacrylate adhesive to the skin surface prior to exposure of the surface to ionizing radiation.

2. References

The following publications, patent applications and patents are cited in this application as superscript numbers:

Sitton, "*Early and Late Radiation-Induced Skin Alterations Part I:Mechanisms of Skin Changes*", Oncology Nursing Forum, 19(5):801–807 (1992)

Sitton, "*Early and Late. Radiation-Induced Skin Alterations Part II:Nursing Care of Irradiated Skin*", Oncology Nursing Forum, 19(6):907–912 (1992)

Dini, et al., "*Management of Acute Radiodermatitis*", Cancer Nursing, 16(5):366–370 (1993)

Barley, "*Methods for Retarding Blister Formation by Use of Cyanoacrylate Adhesives*", U.S. Pat. No. 5,306,490, issued Apr. 26 1994.

Rubin et al., *Clinical Radiation and Pathology*, Chapter 3, Skin and Adnexa, pp. 62–119(1986)

Perez, et al., *Principles and Practice of Radiation Oncology*, Second Edition, J. B. Lippincott Company, Philadelphia, Pa., pp. 104–105(1987)

Barley, et al., *Methods for Treating Suturable Wounds by Use of Sutures and Cyanoacrylate Adhesives*, U.S. Pat. No. 5,254,132, issued Oct. 19, 1993

Robertson, et al., *Fluorocyanoacrylates*, U.S. Pat. No. 3,722,599, issued Mar. 27, 1973

Barley, et al., International Patent Application Publication No. WO 93/25196, for *Methods for Treating Non-Suturable Wounds by Use of Cyanoacrylate Adhesives*, published Dec. 23, 1993

Barley, et al., U.S. patent application Ser. No. 08/200,953, for *Methods for Reducing Skin Irritation From Artificial Devices by Use of Cyanoacrylate Adhesives*, filed Feb. 24, 1994

All of the above publications, patent applications and patents are herein incorporated by reference in their entirety to the same extent as if each individual publication, patent application or patent was specifically and individually indicated to be incorporated by reference in its entirety.

STATE OF THE ART

Treatment regimens for many tumors (e.g., tumors of the head, neck, chest, breasts, prostate, etc.) currently include daily exposure of the tumor to ionizing radiation repeated over a period of time where application of the radiation to the site of the tumor is through the skin.[1] Typical regimens include daily (e.g., five times per week) exposure of the tumor with ionizing radiation for 5 or more weeks wherein both the length of treatment and the total dosage of radiation are dictated by the tumor size, location, etc. For example, treatment regimens for small microscopic tumors typically include daily exposure of the tumor to ionizing radiation for approximately 5 weeks with a cumulative ionizing radiation dosage of about 4500–5000 rads [45–50 Gray (Gy)]. Treatment regimens for larger tumors as well as tumors located in the head and neck typically are extended to 8 or more weeks and can employ a cumulative ionizing radiation dosage of about 7400 or more rads (74 or more Gy). Treatment of tumors located in the head and neck are particularly troublesome because stem cells associated with such tumors will exhibit maximal recruitment of tumor cells approximately half way through the treatment schedule. To compensate for this recruitment, there is some interest in hyperfractionation of the ionizing radiation where the radiation is applied more than once dally to the patient. Hyperfractionation requires, however, that acute radiation-induced skin damage be within tolerable limits during the treatment regimen.[6]

Contrarily, interruptions for any significant period of time in the dally schedule of ionizing radiation reduces the effectiveness of the radiation on the tumor. Moreover, for tumors located in the head and neck, such interruptions can actually exacerbate the cancer by permitting recruitment of tumor cells by stem cells associated with the tumor. Accordingly, maintenance of the daily radiation schedule is clinically significant in effective treatment of the tumor with ionizing radiation.

Notwithstanding the benefits in maintaining the dally schedule of ionizing radiation for the entire length of the prescribed treatment regimen, acute radiation-induced skin injuries, such as erythema, dry desquamation, moist desquamation, epilation and ulceration, often dictate an interruption in this schedule in order to permit the skin to heal sufficiently to resume the dally schedule of ionizing radiation. Such acute radiation-induced skin injuries arise because ionizing radiation has sufficient energy to break chemical bonds thereby degrading/destroying tissues and has a particularly adverse affect on rapidly dividing cells, including the basal cells found at the base of the epidermis.

Basal cells rapidly divide to provide a renewed cell population to compensate for cell lose at the surface of the epidermis. When a basal cell divides, two cells are formed. One of these cells begins the progressive process of terminal differentiation into mature, dead, keratinized or cornified cells. From the outermost layer of the epidermis, cornified cells detach and desquamate. The average turnover time of the entire epidermis is about 3–4 weeks. Accordingly, acute radiation-induced skin conditions arising from damage to basal cell is evident approximately 3–5 weeks after initiation of the ionizing radiation regimen and can continue for approximately 4 weeks after cessation of this regimen.[5]

The degree of skin injury depends on a large number of factors such as the ionizing radiation source, the dose, the treatment schedule, the site of irradiation on the patient, individual sensitivity of the patient, etc. It is estimated, however, that approximately one-third of patients undergoing ionizing radiation therapy for tumors will experience an interruption in the therapy schedule, typically of about 1–2 weeks, to permit the skin to heal sufficiently to resume the therapy. This interruption typically occurs at 3–5 weeks after initiation of the therapy where damage to basal cells in the epidermis manifests itself at the skin surface.

Heretofore, the art has addressed acute radiation-induced skin damage by use of ointments, lotions, powders, occlusive dressings, etc. on the damaged skin.[1,2] Likewise, Dini, et al.[3] discloses the use of a foam emulsion containing hydrophilic (propylene glycol, glycerol and polyunsaturated alcohols) and hydrophobic (stearic acid) components which was applied to radiation-induced damaged skin in order to enhance recovery of the damaged skin.

It is apparent, then, that there is a continuing need in the art of radiation oncology to inhibit the degree of skin damage induced by exposure to ionizing radiation during the treatment regimen.

This invention is directed, in part, to the discovery that application of a layer of cyanoacrylate polymer to the surface of the skin area which is to be exposed to ionizing radiation followed by exposure to ionizing radiation through this layer reduces the degree of acute radiation-induced skin damage in the patient. In addition, late skin effects of radiation therapy that include atrophy, thinning, telangiectasia, fibrosis, altered pigmentation, necrosis, ulceration and carginogenis, etc. may be reduced by application of the layer of cyanoacrylate polymer at the time of radiation treatment and/or at the time late skin effects arise.

Surprisingly, the reduction in the degree of acute radiation-induced skin damage by the cyanoacrylate adhesives is achieved notwithstanding the teaching in the art that tapes (presumably adhesive tapes) should not be applied directly on the treated skin.[2]

The use of cyanoacrylate polymers per this invention is also in contrast to their known medical uses as an alternative or adjunct to sutures[7] or as a hemostat[8]. Other described uses of cyanoacrylate polymers include their use to prevent friction blister formation[4], treating small non-suturable wounds[9], and in inhibiting surface skin irritation arising from friction between the skin surface and artificial devices such as tapes, prosthetic devices, casts, and the like.[10]

SUMMARY OF THE INVENTION

This invention is directed to methods for inhibiting acute and/or late radiation-induced skin damage during treatment of a patient with ionizing radiation by application of a layer of cyanoacrylate adhesive to the surface of the skin area which is to be exposed to ionizing radiation followed by exposure to ionizing radiation through this layer.

Accordingly, in one of its method aspects, this invention is directed to a method for inhibiting acute and/or late radiation-induced skin damage to a human patient during treatment of that patient with ionizing radiation wherein application of the radiation is through a portion of the skin thereby exposing the epidermal layer of that skin portion to said ionizing radiation which method comprises:

(a) applying a layer of cyanoacrylate polymer to the surface of the skin area which is to be exposed to ionizing radiation; and (b) exposing the patient to ionizing radiation through the layer of cyanoacrylate polymer.

The layer of cyanoacrylate polymer is preferably formed from application of cyanoacrylate adhesive onto the skin surface and polymerization of the adhesive in situ prior to exposure to ionizing radiation so as to form an adherent, flexible, waterproof polymer layer over the skin areas to be exposed to the radiation. In a further preferred embodiment, the cyanoacrylate, in monomeric form, is represented by formula I:

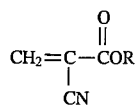

where R is selected from the group consisting of:
alkyl of 2 to 10 carbon atoms,
alkenyl of 2 to 10 carbon atoms,
cycloalkyl groups of from 5 to 8 carbon atoms,
phenyl,
2-ethoxyethyl,
3-methoxybutyl,
and a substituent of the formula:

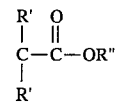

wherein each R' is independently selected from the group consisting of:
hydrogen and methyl, and
R" is selected from the group consisting of:
alkyl of from 1 to 6 carbon atoms,
alkenyl of from 2 to 6 carbon atoms,
alkynyl of from 2 to 6 carbon atoms,
cycloalkyl of from 3 to 8 carbon atoms,
aralkyl selected from the group consisting of benzyl, methylbenzyl and phenylethyl,
phenyl, and
phenyl substituted with 1 to 3 substituents selected from the group consisting of hydroxy, chloro, bromo, nitro, alkyl of 1 to 4 carbon atoms, and alkoxy of from 1 to 4 carbon atoms.

Accordingly, in another of its method aspects, this invention is directed to a method for inhibiting acute and/or late radiation-induced skin damage to a human patient during treatment of that patient with ionizing radiation wherein application of the radiation is through a portion of the skin thereby exposing the epidermal layer of that skin portion to said ionizing radiation which method comprises:

(a) applying to skin surface area(s) which will be exposed to ionizing radiation a sufficient amount of a cyanoacrylate adhesive so as to cover said area(s);

(b) polymerizing the cyanoacrylate adhesive so as to form a flexible, waterproof, adhesive polymer layer which adheres to the area(s) where the adhesive was applied; and (c) exposing the patient to ionizing radiation through the layer of cyanoacrylate polymer wherein the cyanoacrylate adhesive, in monomeric form, is represented by formula I above.

Preferably, in the cyanoacrylates of formula I, R is alkyl of from 2 to 10 carbon atoms and more preferably alkyl of from 2 to 8 carbon atoms. Even more preferably, R is butyl, pentyl or octyl and most preferably, R is n-butyl.

In another preferred embodiment, the cyanoacrylate polymer has a thickness of no more than about 1 millimeters so as to avoid a bolus affect on the skin which would exacerbate the skin damage induced by the radiation. More preferably, the cyanoacrylate polymer has a thickness of from about 0.1 to about 0.5 millimeters and still more preferably from about 0.3 to about 0.5 millimeters.

In a particularly preferred embodiment, the cyanoacrylate adhesive to be applied to the skin has a viscosity of from greater than 1 to about 50,000 centipoise at 20° C. and preferably from about 2 to 1,500 centipoise at 20° C. More preferably, the cyanoacrylate in the cyanoacrylate adhesive is almost entirely in monomeric form and the adhesive has a viscosity of from about 20 to about 100 centipoise at 20° C.

DETAILED DESCRIPTION OF THE PREFERRED EMBODIMENTS

This invention relates to methods for inhibiting acute and/or late radiation-induced skin damage during treatment of a patient with ionizing radiation. However, prior to discussing this invention in further detail, the following terms will first be defined.

Definitions

As used herein, the following terms have the following meanings:

The term "ionizing radiation" refers to radiation commonly employed in the treatment of tumors (whether benign or cancerous) which radiation, either as a large single dosage or as repeated smaller dosages, will cause acute skin damage in at least a portion of the patients exposed to this dosage of radiation. Ionizing radiation includes, by way of example, x-rays, electron beams, γ-rays, and the like.

The term "acute radiation-induced skin damage" refers to the damage to the epidermal layer of the skin caused by either a single large dosage or repeated smaller dosages of ionizing radiation which damage can manifest itself about 3–5 weeks after treatment with ionizing radiation. Acute radiation-induced skin damage is sometimes referred to as early radiation induced skin damage and includes, by way of example, erythema, dry desquamation, moist desquamation, epilation and ulceration. Acute radiation-induced skin damage can be particularly severe in skin folds and areas of high friction, e.g., groin, buttocks, the folds of the breast, neck, etc. and the like.

The term "late radiation-induced skin damage" refers to skin damage arising 6 or more months after termination of the radiation treatment which damage includes, by way of example, atrophy, fibrosis, thinning, telangiectasia, altered pigmentation, ulceration, necrosis and carcinogenesis.

The term "cyanoacrylate adhesive" refers to polymerizable adhesive formulations comprising cyanoacrylate monomers or polymerizable oligomers which in their monomer form are compounds represented by formula I as described above.

Preferably, in formula I, R is an alkyl group of from 2 to 10 carbon atoms including ethyl, n-propyl, iso-propyl, n-butyl, iso-butyl, sec-butyl, n-pentyl, iso-pentyl, n-hexyl, iso-hexyl, 2-ethylhexyl, n-heptyl, octyl, nonyl, and decyl. More preferably, R is butyl, pentyl or octyl and most preferably, R is n-butyl.

These cyanoacrylate adhesives are known in the art and are described in, for example, U.S. Pat. Nos. 3,527,224; 3,591,676; 3,667,472; 3,995,641; 4,035,334; and 4,650,826 the disclosures of each are incorporated herein by reference in their entirety.

A preferred cyanoacrylate adhesive for use in the invention is n-butyl-2-cyanoacrylate.

The cyanoacrylate adhesives described herein rapidly polymerize in the presence of water vapor or tissue protein, and the n-butyl-cyanoacrylate is capable of bonding human skin tissue without causing histoxicity or cytotoxicity.

The term "biocompatible plasticizer" refers to any material which is soluble or dispersible in cyanoacrylate adhesive formulations or in solutions comprising cyanoacrylate polymers, which increases the flexibility of the resulting polymer coating on the skin surface, and which is compatible with the skin as measured by the lack of skin irritation. Suitable plasticizers are well known in the art and include those disclosed in U.S. Pat. Nos. 2,784,127 and 4,444,933 the disclosures of both of which are incorporated herein by reference in their entirety. Specific plasticizers include, by way of example only, acetyl tri-n-butyl citrate, butyl benzyl phthalate, dibutyl phthalate, diethyl phthalate, dimethyl phthalate, dioctylphthalate, n-butyryl tri-n-hexyl citrate, benzoate esters of di- and poly-hydroxy branched aliphatic compounds, tri(p-cresyl) phosphate, and the like. The particular plasticizer employed is not critical and preferred plasticizers include alkyl phthalates independently having from 1 to 10 carbon atoms in each alkyl group. A particularly preferred plasticizer is dioctylphthalate.

Methods

The methods of this invention comprise application of a layer of cyanoacrylate polymer onto surface skin areas prior to exposure to ionizing radiation. The cyanoacrylate layer or coating can be applied onto the skin surface as a polymer solution or as prepolymeric formulation comprising polymerizable cyanoacrylate monomers and oligomers.

When a polymer solution is employed, a requisite amount of the solution is applied to the skin surface and, upon removal of the solvent, a layer of polymer is formed thereon. In this embodiment, the thickness of the polymer layer is controlled by the concentration of the polymer in solution and the amount of solution applied to the skin. Such factors are well within the skill of the art.

Suitable solvents include:, by way of example, acetone, methyl ethyl ketone, ethanol and the like. The solution can further comprise a biocompatible plasticizer and other optional additives. Typically, the solution will comprise, from about 1 to about 10 weight percent of a cyanoacrylate polymer based on the total weight of the solution.

In a preferred embodiment, however, a prepolymeric formulation comprising polymerizable cyanoacrylate monomers and/or oligomers (i.e., cyanoacrylate adhesive) is employed. Upon application of the cyanoacrylate adhesive, the surface skin moisture, tissue protein, and temperature are sufficient to initiate polymerization of the adhesive upon application. Thereafter, the skin surface is maintained under suitable conditions to allow polymerization to proceed to formation of the polymer layer. In general, the particular length of time required for polymerization will vary depending on factors such as the amount of adhesive applied, the temperature of the skin, the moisture content of the skin, the surface area of skin to which the adhesive was applied, and the like. However, in a preferred embodiment, polymerization is generally complete within about 10 to about 60 seconds while the skin is maintained at ambient conditions. During this period, the person to whom application of the cyanoacrylate adhesive has been made merely allows the adhesive to form a polymer layer while minimizing any action to prevent the adhesive from being dislodged from that portion of the skin where it was applied or to adhere to unintended objects.

Whether the polymer layer is formed from a solution comprising the polymer or by in situ polymerization of the cyanoacrylate adhesive on the skin surface, sufficient amounts of applied composition are employed to cover (i.e., coat) the entire surface skin area to be exposed to ionizing radiation with a layer of the cyanoacrylate polymer. Preferably, the layer is extended beyond the area to be exposed by preferably at least about 1 centimeter and more preferably by at least about 5 centimeters. If necessary., excess cyanoacrylate polymer can be removed with acetone (nail polish remover) which can be readily conducted except in the case where the adhesive polymer binds to a sensitive skin part (e.g., the eye lids) where it should be removed by a health After formation of the polymer layer on the surface of the skin, the polymer adheres to the skin, is flexible and waterproof, thereby forming a protective coating which enhances the integrity of the underlying skin. Adherence to the skin is enhanced by in situ formation of the polymer layer from the cyanoacrylate adhesive.

While not being limited to any theory, we believe that the polymer layer further inhibits acute radiation-induced skin damage by minimizing moisture loss to the covered skin areas and by preventing frictional contact of the covered skin with, for example, clothing. By inhibiting initial skin damage, further and more acute skin damage due to the inflammatory response of the initial skin damage is prevented. Additionally, we further believe that inhibition of acute radiation-induced skin damage will result in inhibition of late radiation-induced skin damage.

In general, the polymer layer will adhere to the skin for a period of about 2–4 days after which time it sloughs off. Accordingly, the polymer layer need not be removed in the manner of other adhesives/dressings whose removal results in skin irritation.

The polymer layer is formed over the skin surface prior to exposure of that surface with ionizing radiation. Preferably, the polymer layer is maintained during periods between radiation exposure merely by reapplication of the layer as necessary in the manner described above. In a particularly preferred embodiment, the polymer layer is maintained continuously throughout the period of ionizing radiation treatment. Moreover, because damage to the basal cells of the epidermis can manifests itself up to 4 weeks after termination of the treatment, the polymer layer is preferably maintained for up to 4 weeks after treatment termination.

The polymer layer should be maintained in a unbroken manner over the entire skin area to be exposed to ionizing radiation. This can be assured by careful application of the polymer (either as a polymer solution or as the polymerizable monomer or oligomer) onto the skin. Additionally, the use of a plasticizer will facilitate the maintenance of the polymer coating in an unbroken manner.

In a preferred embodiment, after application of the initial polymer layer, a second, preferably thinner, layer is applied over the coating. Additional amounts of cyanoacrylate adhesive can be applied as needed to maintain an unbroken coating covering over the surface skin areas.

Application is conducted under conditions wherein the polymer layer :has a thickness of no more than about 1 millimeters and preferably has a thickness of from about 0.1 to about 0.5 millimeters. Such a thickness will ensure that the polymer does not act in the manner of a bolus. The amount of cyanoacrylate composition applied to obtain this thickness is well within the skill of the art.

The polymer layer applied onto the skin surface area can be readily controlled by the amount of adhesive or polymer solution packaged in a single dose product or by use of a multiple use dispenser which governs the amount of material applied onto a unit area of surface skin. In this regard, the dispenser described by Otake, U.S. Pat. No. 4,958,748, which is incorporated by reference in its entirety, is particularly advantageous because it dispenses the adhesive or polymer solution in a controlled dropwise manner. Other methods for the controlled dispersement of the cyanoacrylate adhesive include, by way of example, a spray applicator, a brush or solid paddle applicator, applicators for repeated and intermittent use of the cyanoacrylate composition and the like.

A preferred applicator for repeated and intermittent usage is an applicator suitable for the non-sterile storage and metered dispersement of the composition after opening of the applicator wherein the applicator is characterized as having a resealable opening of no more than about 0.008 square inches (0.0516 square centimeters) so as to permit the metered dispersement of the composition from the applicator and which is capable of multiple administrations of the composition and is further characterized as having resealing means such as a cap which either tightly mates with the applicator or which screws onto the applicator.

Preferably, the opening of the applicator is about 0.0016 to about 0.033 square inches (about 0.0103 to about 0.0194 square centimeters).

In another preferred embodiment, the walls of the applicator are made, of a pliable material, so that upon application of pressure onto the walls, the walls depress sufficiently to force the composition contained in the applicator through the opening. Preferably, the applicator is manufactured with its opening covered by a metal foil or other similar construction which closes this opening until the device is ready for use. The opening is then reinstated by use of a pin or similar device which punctures the covering.

In applicators suitable for repeated intermittent uses, the alkyl cyanoacrylate composition is stored at ambient conditions and can be selected to be bacteriostatic. See, for example, Rabinowitz et al., U.S. Pat. No. 3,527,224. When the selected composition is bacteriostatic, prolonged storage at ambient conditions is without regard to the sterility of the formulation because there is no adverse buildup of bacteria during storage.

Because the cyanoacrylate polymer layer is waterproof, the patient is not prevented from bathing and other activities involving exposure to water during the period the polymer layer protects this skin area.

In a preferred but optional embodiment, the methods described herein can be used in conjunction with conventional treatment regimens to inhibit and/or treat acute radiation-induced skin damage. For example, conventional. anti-inflammatory agents, e.g., steroids, can be applied to the skin prior to application of the cyanoacrylate adhesive.

Alternatively, it is contemplated that the anti-inflammatory agent can be incorporated into the cyanoacrylate composition whereupon it will be released into/onto the skin over time. Suitable anti-inflammatory agents include, by way of example, anti-inflammatory steroids well known in the art which steroids include hydrocortisone ( 11,17,21-trihydroxypregn-4-ene-3,20-dione), betamethasone (9-fluoro- 11,17,21-trihydroxy- 16-methylpregna- 1,4-diene-3,20-dione), clobetasone (21-chloro-9-fluoro- 11,17-dihydroxy- 16-methylpregna- 1,4- diene-3,20-dione), clobetasone (21-chloro-9-fluoro-17-hydroxy-16- methylpregna-l,4-diene-3, 11,20-trione), and the like. The anti-inflammatory agent is incorporated into the cyanoacrylate composition in sufficient quantities such that, upon application of the cyanoacrylate polymer layer to the skin, the anti-inflammatory agent will be released in sufficient quantities into/onto the skin as to be therapeutically effective.

Compositions

The polymer or prepolymer (adhesive) compositions described herein are prepared by conventional methods of mixing the appropriate components until homogenous.

The specific viscosity of these compositions depends, in part, on the intended application of the composition. For example, relatively low viscosities are often preferred where application is to be made to a large surface area. This preference results from the fact that those forms are less viscous and, accordingly, will permit more facile large surface area application of a thin application. Contrarily, where application is to be made to a specific position on the skin, higher viscosity materials are preferred to prevent "running" of the material to unintended locations.

Accordingly, these compositions have a viscosity of from about 2 to 50,000 centipoise at 20° C. A thickening agent is optionally employed to increase the viscosity of the composition which thickening agent is any biocompatible material which increases the viscosity of the composition whether as a prepolymer composition or as a polymeric composition. Suitable thickening agents include, by way of example, polymethyl methacrylate (PMMA) or other preformed polymers soluble in the alkyl cyanoacrylate, a suspending agent such as fumed silica and the like with PMMA being preferred. Fumed silica is particularly useful in producing a gel for topical application having a viscosity of from about 1500 to 50,000. Suitable thickening agents for prepolymeric compositions also include a partial polymer of the alkyl cyanoacrylate as disclosed in U.S. Pat. Nos. 3,654,239 and 4,038,345 both of which are incorporated herein by reference in their entirety.

Thickening agents are deemed to be biocompatible if they are both soluble in the alkyl cyanoacrylate composition and are compatible with the skin as measured by the lack of skin irritation.

The composition preferably includes a biocompatible plasticizer such plasticizers are preferably included from about 10 to 30 weight percent and more preferably from about 18 to 25 weight percent based on the total weight of the composition.

Additionally, in prepolymeric compositions, a polymerization inhibitor is also preferably employed and, in a particularly preferred embodiment, this inhibitor is sulfur dioxide which is employed at from about 50 to 500 ppm based on the total weight of the composition.

The compositions may additionally contain one or more optional additives such as colorants, perfumes, anti-diffusion agents, rubber extenders, modifying agents, etc. In practice, each of these optional additives should be both miscible and compatible with the cyanoacrylate adhesive and the polymer resulting therefrom. Compatible additives are those that do not prevent the use of the cyanoacrylate adhesives and the resulting polymers in the manner described herein.

In general, colorants are added so that the polymeric film will contain a discrete and discernable color. Perfumes are added to provide a pleasant smell to the formulation. Rubber extenders are added to further enhance the flexibility of the resulting polymer layer. The amount of each of these optional additives employed in the cyanoacrylate adhesive composition is an amount necessary to achieve the desired effect.

Additional compositions useful in the practice of this invention are disclosed by Greff, et al., U.S. patent application Ser. No. 08/299,993, which application is incorporated herein by reference in its entirety.

Utility

The methods described herein are useful in inhibiting acute radiation-induced skin damage during radiation treatment of malignant and benign tumors as well as late radiation-induced skin damage. Such tumors include, by way of example only, tumors associated with breast cancer, tumors associated with prostate cancer, tumors associated with rectal cancer, brain tumors, tumors associated with lymph node cancer, and any other tumors where ionizing radiation forms a part of the treatment regimen.

These methods are particularly useful in prophylactic methods to inhibit the skin damage due to radiation treatment by either reducing the severity of the skin damage and/or by delaying the onset of the damage. These methods can also be used with skin irritated by ionizing radiation but yet unbroken to inhibit the onset of more severe skin damage or to reduce the severity thereof.

The following example illustrates certain embodiments of the invention but is not meant to limit the scope of the claims in any way.

EXAMPLE

The treatment regimen for a female patient, age 49, suffering from an in situ breast cancer in the right breast included daily (5 times per week) radiation treatments of the breast. The radiation protocol comprises 28 sessions of 180 rads (1.8 Gy) of X-ray photon radiation to the whole breast over approximately a 6 week period. The radiation was spatially applied equally from the left and right directions of the breast. Following this treatment, an additional 5 treatments were given to the original tumor site using an electron beam [200 rads (2 Gy)]. All treatments were given using a Siemans Mevatron 12 linear accelerator.

Prior to each day of radiation treatment, the patient applied a cyanoacrylate adhesive formulation comprising n-butyl α-cyanoacrylate in monomeric form, 20 weight percent of dioctyl phthalate as a plasticizer and 200 ppm $SO_2$ over the entire breast and then allowed this composition to polymerize whereby a polymer layer was formed. Upon completion of the treatment procedure, the patient exhibited little, if any, skin damage during the treatment and was able to complete the treatment without interruption.

From the foregoing description, various modifications and changes in the composition and method will occur to those skilled in the art. All such modifications coming within the scope of the appended claims are intended to be included therein.

What is claimed is:

1. A method for inhibiting acute radiation-induced skin damage to a patient arising from treatment of that patient with ionizing radiation wherein application of the radiation is through a portion of the skin thereby exposing the epidermal layer of that skin portion to said ionizing radiation which method comprises:

(a) applying a layer of cyanoacrylate polymer to the surface of the skin area which is to be exposed to ionizing radiation; and (b) exposing the patient to ionizing radiation through the layer of cyanoacrylate polymer.

2. The method according to claim 1 wherein the treatment comprises exposing the patient to ionizing radiation up to 5 times per week over 4–10 weeks.

3. The method according to claim 1 wherein said layer of cyanoacrylate polymer is maintained over the skin throughout the entire treatment period.

4. The method according to claim 3 wherein said layer of cyanoacrylate polymer is maintained over the skin for up to 4 weeks after exposure to ionizing radiation terminates.

5. The method according to claim 1 wherein said cyanoacrylate polymer, in monomeric form, is selected from the group consisting of octyl cyanoacrylate and butyl cyanoacrylate.

6. The method according to claim 5 wherein said cyanoacrylate polymer, in monomer form, is n-butyl cyanoacrylate.

7. The method according to claim 1 wherein said polymer further comprises a biocompatible plasticizer.

8. The method according to claim 7 wherein said biocompatible plasticizer is dioctyl phthalate.

9. The method according to claim 7 wherein said polymer still further comprises a polymerization inhibitor.

10. The method according to claim 9 wherein said polymerization inhibitor is $SO_2$.

11. The method according to claim 1 wherein the polymer layer has a thickness of no more than about 1 millimeters.

12. A method for inhibiting acute and/or late radiation-induced skin damage to a patient arising from treatment of that patient with ionizing radiation wherein application of the radiation is through a portion of the skin thereby exposing the epidermal layer of that skin portion to said ionizing radiation which method comprises:

(a) applying to skin surface area(s) which will be exposed to ionizing radiation a sufficient amount of a cyanoacrylate adhesive so as to cover said area(s);

(b) polymerizing the cyanoacrylate adhesive so as to form a flexible, waterproof, adhesive polymer layer which adheres to the area(s) where the adhesive was applied; and (c) exposing the patient to ionizing radiation through the layer of cyanoacrylate polymer wherein the cyanoacrylate adhesive, in monomeric form, is represented by formula I:

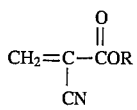

where R is selected from the group consisting of:
alkyl of 2 to 10 carbon atoms,
alkenyl of 2 to 10 carbon atoms,
cycloalkyl groups of from 5 to 8 carbon atoms,
phenyl,
2-ethoxyethyl,
3-methoxybutyl,
and a substituent of the formula:

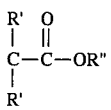

wherein each R' is independently selected from the group consisting of:
hydrogen and methyl, and
R" is selected from the group consisting of:
alkyl of from 1 to 6 carbon atoms,
alkenyl of from 2 to 6 carbon atoms,
alkynyl of from 2 to 6 carbon atoms,
cycloalkyl of from 3 to 8 carbon atoms,
aralkyl selected from the group consisting of benzyl, methylbenzyl and phenylethyl,
phenyl, and
phenyl substituted with 1 to 3 substituents selected from the group consisting of hydroxy, chloro, bromo, nitro, alkyl of 1 to 4 carbon atoms, and alkoxy of from 1 to 4 carbon atoms.

13. The method according to claim 12 wherein the treatment comprises exposing the patient to ionizing radiation up to 5 times per week over 4–10 weeks.

14. The method according to claim 12 wherein said layer of cyanoacrylate polymer is maintained over the skin throughout the entire treatment period.

15. The method according to claim 14 wherein said layer of cyanoacrylate polymer is maintained over the skin for up to 4 weeks after exposure to ionizing radiation terminates.

16. The method according to claim 12 wherein R is selected from the group consisting of octyl and butyl.

17. The method according to claim 16 wherein R is n-butyl.

18. The method according to claim 12 wherein said polymer comprises a biocompatible plasticizer.

19. The method according to claim 18 wherein said biocompatible plasticizer is dioctyl phthalate.

20. The method according to claim 18 wherein said polymer further comprises a polymerization inhibitor.

21. The method according to claim 20 wherein said polymerization inhibitor is $SO_2$.

22. The method according to claim 12 wherein the polymer layer has a thickness of no more than about 1 millimeters.

* * * * *

UNITED STATES PATENT AND TRADEMARK OFFICE
CERTIFICATE OF CORRECTION

PATENT NO. : 5,554,365

DATED : September 10, 1996

INVENTOR(S) : Michael M. Byram, et al.

It is certified that an error appears in the above-identified patent and that said Letters Patent is hereby corrected as shown below:

<u>ON THE TITLE PAGE</u>:
```
     [75]  Inventors:
                     change "Yorba Linda, both of Calif." to
     --St. Petersburg, Florida--; and change "Littleton, Colo." to
     --Colorado Springs, Colo.--;

On column 6,
       line 59, kindly insert --care professional.-- at the end of
       the line;
On column 8,
       line 2, kindly delete "0.033" and insert --0.003--
       therefor;
       line 39, kindly delete "clobetasone" and insert
       --clobetasol-- therefor.
```

Signed and Sealed this

Fourth Day of February, 1997

Attest:

BRUCE LEHMAN

*Attesting Officer*　　　*Commissioner of Patents and Trademarks*